United States Patent [19]

Gerber

[11] 4,208,794
[45] Jun. 24, 1980

[54] SET OF ARTIFICIAL MOLAR TEETH
[75] Inventor: Albert Gerber, Zürich, Switzerland
[73] Assignee: Dentalgerate "Condylator" Peter T. Gerber, Zürich, Switzerland
[21] Appl. No.: 830,999
[22] Filed: Sep. 6, 1977
[30] Foreign Application Priority Data
Oct. 12, 1976 [CH] Switzerland .................. 12878/76
[51] Int. Cl.$^2$ .............................................. A61C 13/00
[52] U.S. Cl. .................................................. 433/197
[58] Field of Search ................................. 32/2, 8, 32
[56] References Cited
U.S. PATENT DOCUMENTS
3,105,300 10/1963 Beresin ........................... 32/32
3,305,926 2/1967 Gerber ............................. 32/2

Primary Examiner—Louis G. Mancene
Assistant Examiner—Michael J. Foycik, Jr.
Attorney, Agent, or Firm—O'Brien & Marks

[57] ABSTRACT

A set of artificial molar teeth composed of two respective upper and two respective lower premolars and two respective upper and two respective lower molars, wherein at each pair of superimposed teeth the one tooth has a mastication furrow or groove and the other tooth at the side of the gum possesses a protuberance coacting with the mastication groove of the one tooth. In order to realize successive contact of the teeth of the first premolars to the second molars there is provided a stepped reduction of the tooth angle and/or a stepped reduction in the size of the friction path.

1 Claim, 5 Drawing Figures

SET OF ARTIFICIAL MOLAR TEETH

BACKGROUND OF THE INVENTION

The present invention relates to a new and improved set of artificial molar teeth.

The applicant of this development has sometime ago developed a particular shape of artificial molar teeth and also patented the same in Swiss Pat. No. 405,601, corresponding to U.S. Pat. No. 3,305,926, to which reference may be readily had. These prior art artificial teeth have been continuously fabricated. During the course of the manufacture thereof there have been undertaken improvements which are more of an unimportant nature, primarily concerning the appearance of such teeth.

SUMMARY OF THE INVENTION

Hence, it is a primary object of the present invention to improve the chewing or mastication efficiency of these heretofore known molar teeth.

Still a further significant object of the present invention aims at a new and improved construction of artificial molar teeth possessing a novel coaction and improved chewing efficiency.

What is considered to be novel with the artificial molar teeth of this development is that they are designed to carry out a successive contact which is comparable to the cutting action of a scissor. Consequently, there is eliminated the otherwise conventional group contact which is present by virtue of the natural action of the teeth. With the so-called group contact, during chewing of soft foods, there come into contact at the relevant chewing side all antagonistic premolars and molars at the same time, and thus such action is referred to also as "simultaneous contact".

During the chewing of fibrous foodstuffs (meat and a number of types of vegetables) the same premolars and molars again are employed as a closed group, and therefore, are extremely inefficient for cutting through the fibrous structure. However, if in daily life one is concerned with the application of minimum forces to fibrous materials, for instance, textile fabrics, then a scissor is used with its successive contact, because thereby it is possible to cut "fiber after fiber".

Now since the wearer of artificial teeth during eating must transmit the forces developed by the mastication muscular system through the agency of sensitive tissue (periosteum and mucous membrane) from the jawbone to the artificial teeth, the user is at a considerable drawback in relation to humans having natural teeth. Consequently, a great number of individuals who wear artificial teeth avoid eating foods which contain chewing-resistant fibers or only insufficiently finely comminute or chew the same or sometimes never sufficiently finely chew the same, then swallowing such improperly chewed food. In a simple comparison, when chewing with group contact the action which prevails is such as if a tailor were to cut textiles with a mincing or chopping knife (for instance for group contact) instead of with a scissors (for instance for successive contact). While taking into account this simple comparison, it would be possible to consider the term "successive contact" also as "scissor contact" or "principle of the scissor function realized by successive contact of the premolar-molar row".

In conjunction with the heretofore known basic construction, as the same has been described in the aforementioned Swiss Pat. No. 405,601 and U.S. Pat. No. 3,305,926, the disclosures of which are incorporated herein by reference, at the upper premolars and molars the downwardly outwardly sloping or inclined inner surfaces (the so-called work bevels or facets) are modified with regard to the size of the workpath and their angle of attack in the following manner:

The work bevel with the steepest angle of attack and the longest sliding path is incorporated at the first upper premolar. With decreasing slope of the angle of attack and decreasing length of the sliding path there then follow the work bevels at the second upper premolar, at the first molar and then at the second molar. The aforementioned modification results in that in conjunction with each combined grinding-closing movement, fibrous foodstuffs are not, as was heretofore conventional, acted upon with a punching action requiring a great expenditure of force for the simultaneous working of all of the premolars and molars, rather increasingly so and with an improved comminution effect with successive contact possessing a shearing action. The improved chewing or mastication efficiency can be proven by chewing tests.

When equipping unfavorable jaw conditions with a total set of artificial teeth or dentures the utilization of buccal protuberances in the molar region increases quite considerably for the chewing function the danger of lateral tilting of the upper artificial denture. The buccal protuberances of the upper molars must therefore quite often be reduced, possibly totally ground. Yet, in order to insure that the principle of successive contact also prevails during the chewing movements, also then when the previously mentioned protuberances must be reduced or totally ground, the successive contact at the work region of the first and second molars must be automatically assumed by the lingual protuberances of the upper molar and their friction at the associated slide surfaces of the lower molars.

DETAILED DESCRIPTION OF THE DRAWING

DETAILED DESCRIPTION OF THE PREFERRED EMBODIMENTS

Due to intentional modifications at the artificial premolars and molars which have been protected by the aforementioned Swiss Pat. No. 405,601 of the instant application, and the corresponding U.S. Pat. No. 3,307,926, it is possible to generally considerably improve the chewing effect of these teeth and, in particular, their comminution effect for fiberous-containing foods (meat, salad and other vegetables).

This improvement is achieved due to the employment of the novel successive contact possible with the artificial teeth of the invention, instead of the anatomical underscored and strived for worldwide group contact of the artificial teeth. Considered from the constructional standpoint the successive contact is predicated upon a reduction of the tooth angle or angle of inclination 10 of inclined contact surface 12 and/or a likewise stepped reduction of the size of the friction path or length 14 of surface 12 proceeding from the first premolar to the second molar. This friction path is located at the buccal protuberance of the upper premolars. At the molar region the fiction path is selectively disposed likewise at the buccal protuberances of the upper or at the lingual protuberances of the lower molars.

Figure 1:
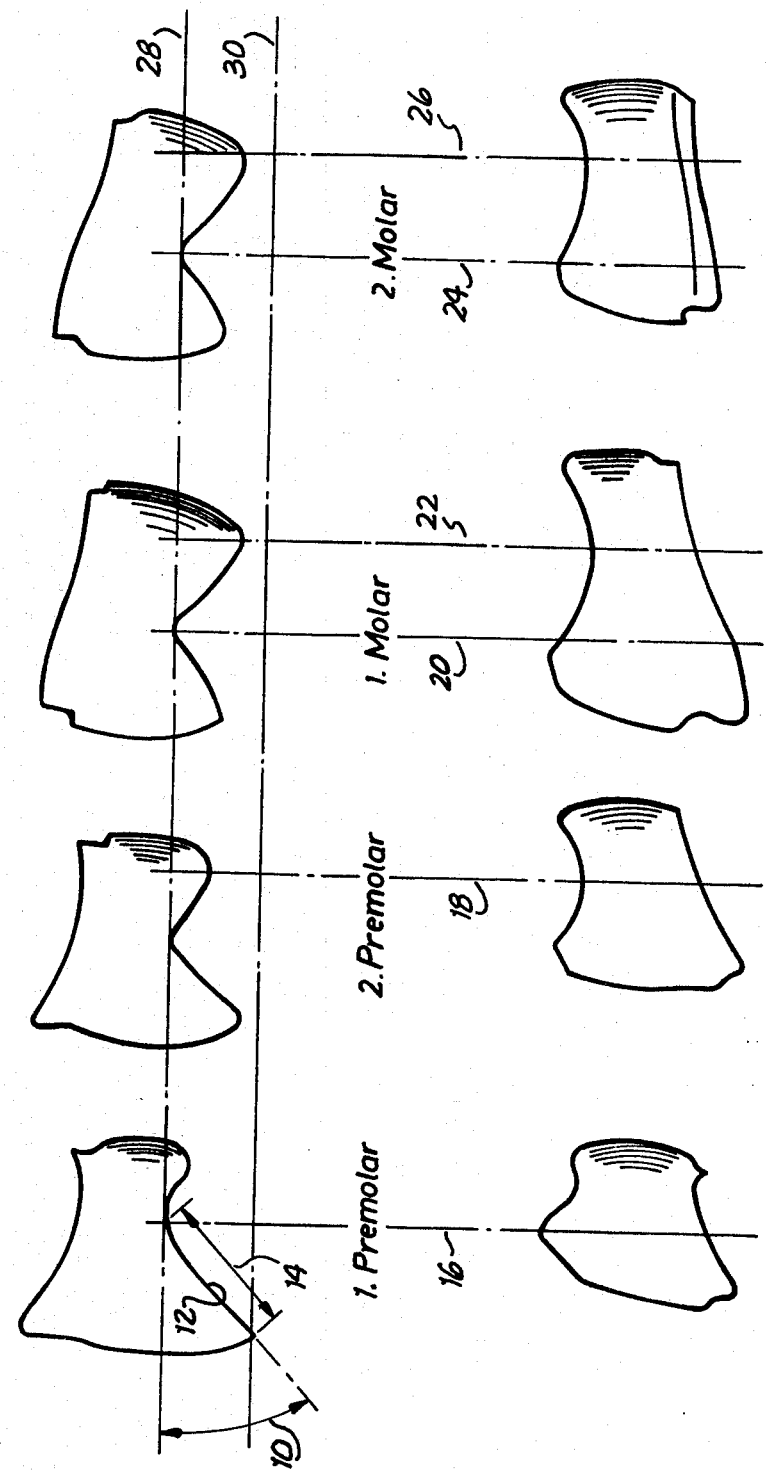
FIG. 1 is a side elevational view of the protruding tooth portions of the premolars and molars for one side of a set of artificial teeth, the tooth portions being shown in spaced relationship.
Figure 2:
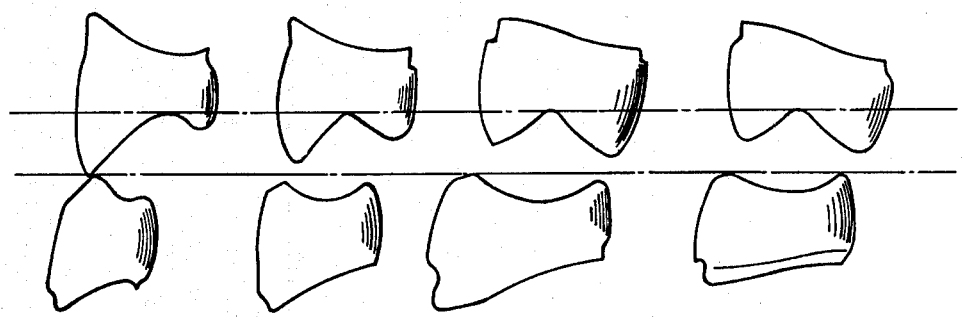
FIG. 2 is a view similar to FIG. 1 but with the upper and lower teeth portions in a first occluding position.
Figure 3:
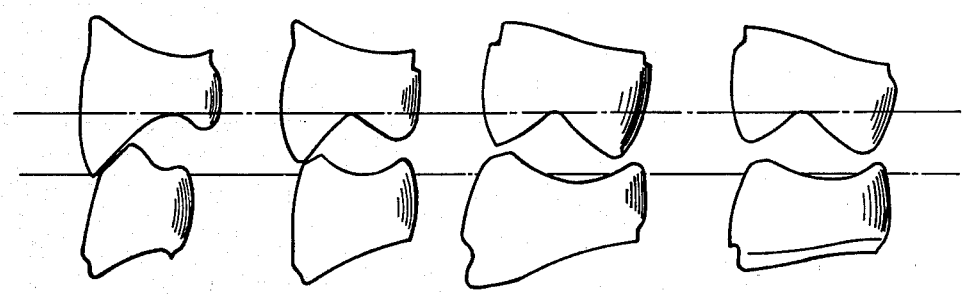
FIG. 3 is a view similar to FIGS. 1 and 2 but with the upper and lower teeth portions in a second occluding position.
Figure 4:
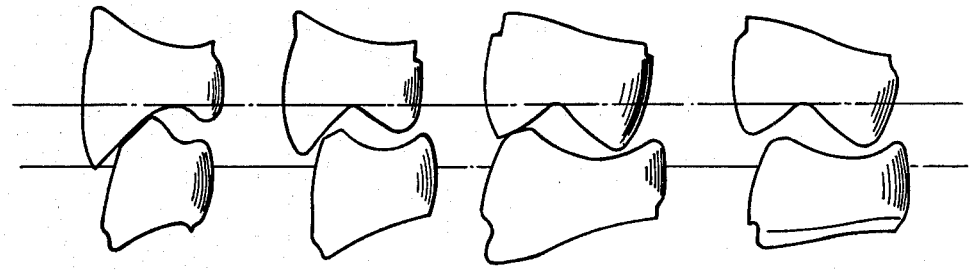
FIG. 4 is a view similar to FIGS. 1, 2 and 3 but with the upper and lower teeth portions in a third occluding position.
Figure 5:
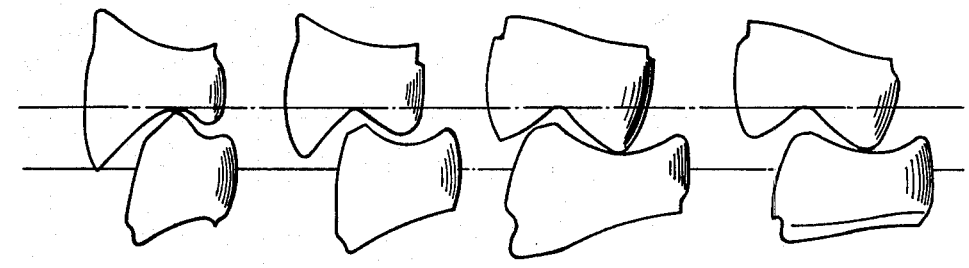
FIG. 5 is a view similar to FIGS. 1, 2, 3 and 4 but with the upper and lower teeth portions in a fourth occluding position.

The premolar and molar teeth portions in each of the upper and lower sets are shown spaced apart for purposes of illustration in FIGS. 1-5, but in an actual set of artificial teeth, the premolars and molars are much closer together as is well known in the art. Vertical lines 16, 18, 20, 22, 24 and 26 indicate one relative position of the upper and lower sets of teeth. Horizontal line 28 illustrates the general horizontal relative positioning of the upper teeth, the line 28 extending generally along the deepest points of the furrows in the upper teeth. Horizontal line 30 illustrates the general position of protuberances of the lower teeth at a first occluding position shown in FIG. 2. The successive contact of the first premolars, the second premolars, the first molars and the second molars are illustrated in FIGS. 2-5, respectively.

While there are shown and described present preferred embodiments of the invention, it is to be distinctly understood that the invention is not limited thereto, but may be otherwise variously embodied and practiced within the scope of the following claims. Accordingly,

What is claimed is:

1. In a set of artificial posterior teeth including first and second upper premolars, first and second lower premolars, first and second upper molars, and first and second lower molars, arranged in respective pairs of upper and lower generally superimposed teeth wherein one tooth of each pair of upper and lower teeth has an inclined contact surface defining a mastication groove, and the other tooth of each pair of upper and lower teeth has a proturberance coacting with the contact surface of the one tooth, the improvement comprising
    said inclined contact surfaces of the respective one teeth having successive lesser angles of inclination proceeding from the one first premolar tooth to the one second molar tooth,
    said inclined contact surfaces of the respective one teeth having successive lesser lengths proceeding from the one first premolar tooth to the one second molar tooth, and
    said contact surfaces and said protuberances on the upper and lower teeth having respective relative heights and positions such that there is successive contact between the coacting protuberances and contact surfaces of the first premolars, the second premolars, the first molars and the second molars in the named order.

* * * * *